(12) United States Patent
Schneider et al.

(10) Patent No.: US 9,863,849 B2
(45) Date of Patent: Jan. 9, 2018

(54) METHOD FOR OPERATING A GAS SENSOR ELEMENT AND DEVICE FOR CARRYING OUT SAID METHOD

(75) Inventors: Jens Schneider, Leonberg (DE); Helge Schichlein, Stuttgart (DE); Frank Stanglmeier, Eberdingen-Hochdorf (DE); Lothar Diehl, Gemmrigheim (DE); Eckart Reihlen, Engels (RU)

(73) Assignee: ROBERT BOSCH GMBH, Stuttgart (DE)

( * ) Notice: Subject to any disclaimer, the term of this patent is extended or adjusted under 35 U.S.C. 154(b) by 275 days.

(21) Appl. No.: 14/111,525

(22) PCT Filed: Feb. 17, 2012

(86) PCT No.: PCT/EP2012/052735
§ 371 (c)(1),
(2), (4) Date: Feb. 14, 2014

(87) PCT Pub. No.: WO2012/139797
PCT Pub. Date: Oct. 18, 2012

(65) Prior Publication Data
US 2014/0157869 A1    Jun. 12, 2014

(30) Foreign Application Priority Data

Apr. 15, 2011 (DE) .................. 10 2011 007 447

(51) Int. Cl.
*G01M 15/10* (2006.01)
*G01N 33/00* (2006.01)
*F01N 11/00* (2006.01)

(52) U.S. Cl.
CPC .......... *G01M 15/102* (2013.01); *F01N 11/00* (2013.01); *G01N 33/007* (2013.01)

(58) Field of Classification Search
CPC ............ G01N 27/417; G01N 27/4071; G01N 27/4067; G01N 27/4074; G01N 27/419;
(Continued)

(56) References Cited

U.S. PATENT DOCUMENTS 5,709,198 A    1/1998   Sagisaka et al.
6,009,866 A    1/2000   Sagisaka et al.
(Continued)

FOREIGN PATENT DOCUMENTS

DE    196 12 387    10/1996
DE    100 49 685    4/2002
(Continued)

OTHER PUBLICATIONS

International Search Report, PCT International Application No. PCT/EP2012/052735, dated Aug. 10, 2012.
(Continued)

*Primary Examiner* — Randy Gibson
*Assistant Examiner* — Gedeon M Kidanu
(74) *Attorney, Agent, or Firm* — Norton Rose Fulbright US LLP; Gerard Messina

(57) ABSTRACT

A method for operating at least one sensor element for detecting at least one property of a gas in a measured-gas space is described. The method comprises at least the following steps: at least one first step, in the first step at least one parameter being ascertained; at least one second step, in the second step the parameter being compared with at least one comparison value, in accordance with that comparison at least one feature being allocated to the sensor element or to at least one part of the sensor element. An apparatus for carrying out the method is also described.

26 Claims, 1 Drawing Sheet

(58) Field of Classification Search
CPC . G01N 33/007; F01N 11/007; F01N 2550/02; F01N 11/00; F02B 1/04; F02D 41/1475; F02D 41/1476; F02D 41/1494; F02D 2041/228; F02D 2200/501; F02D 41/123; F02D 41/1446; F02D 41/1454; F02D 41/1495; G05D 23/1909; G05D 23/24
See application file for complete search history.

(56) References Cited

U.S. PATENT DOCUMENTS

| | | | |
|---|---|---|---|
| 6,314,790 B1 | 11/2001 | Sagisaka et al. | |
| 7,332,719 B2 | 2/2008 | Frodl | |
| 7,596,993 B2* | 10/2009 | Fukagai | F02D 41/1456 73/114.72 |
| 8,343,322 B2* | 1/2013 | Wahl | B65D 1/0215 204/406 |
| 8,361,306 B2* | 1/2013 | Teramoto | G01N 27/419 204/424 |
| 8,394,248 B2* | 3/2013 | Kobayashi | G01N 27/4074 204/424 |
| 8,404,101 B2* | 3/2013 | Sasaki | G01N 27/4071 204/424 |
| 8,538,665 B2 | 9/2013 | Wagner | |
| 2004/0238378 A1* | 12/2004 | Kumazawa | G01N 27/4175 205/781 |
| 2006/0219553 A1* | 10/2006 | Ieda | G01N 33/007 204/424 |
| 2007/0010932 A1* | 1/2007 | Gotoh | F01N 11/00 701/114 |
| 2007/0119708 A1* | 5/2007 | Oya | G01N 27/4175 204/401 |
| 2008/0289961 A1* | 11/2008 | Schmitt | G01N 27/4071 204/424 |
| 2009/0064758 A1* | 3/2009 | Walter | F02D 41/123 73/23.31 |
| 2009/0145778 A1* | 6/2009 | Allmendinger | G01N 27/419 205/789 |
| 2009/0164091 A1* | 6/2009 | Kobayashi | G01N 27/4074 701/102 |
| 2011/0146379 A1* | 6/2011 | Kilinc | G01N 27/4175 73/23.31 |
| 2012/0167656 A1* | 7/2012 | Verdier | G01N 27/4175 73/1.06 |
| 2013/0327124 A1* | 12/2013 | Schneider | F01N 11/007 73/25.01 |
| 2014/0033794 A1* | 2/2014 | Reinhardt | G01N 27/4065 73/1.06 |
| 2015/0039256 A1* | 2/2015 | Michalske | F02D 41/1454 702/104 |

FOREIGN PATENT DOCUMENTS

| | | | |
|---|---|---|---|
| DE | 20 2005 015 023 | 12/2005 | |
| DE | 10 2005 020 864 | 11/2006 | |
| DE | 10 2008 062 626 | 6/2009 | |
| DE | 10 2007 062 800 | 7/2009 | |
| DE | 10 2008 011 256 | 9/2009 | |
| DE | 10 2008 020 651 | 12/2009 | |
| DE | 10 2009 000 457 | 7/2010 | |
| DE | 102009027378 A1 * | 1/2011 | ........ F02D 41/1495 |
| DE | 10 2009 045 367 | 4/2011 | |
| EP | 1 707 950 | 10/2006 | |
| JP | 60 218 058 | 10/1985 | |

OTHER PUBLICATIONS

Robert Bosch GmbH, "Sensoren im Kraftfahrzeug," 1st Edition, pp. 160-165, 2010.
Hatech Gasdetectietechniek BV: "MX2100—Handleiding bij gebruik en onderhoud," May 21, 2008 (http://www.hatechgas.com/documents/view/3730) (retrieved on Aug. 2, 2012).

* cited by examiner

METHOD FOR OPERATING A GAS SENSOR ELEMENT AND DEVICE FOR CARRYING OUT SAID METHOD

BACKGROUND INFORMATION

Sensor elements for detecting at least one property of a gas in a measured-gas space are available. The present invention is explained below, with no limitation of further possible embodiments, substantially with reference to methods and apparatuses that serve for quantitative and/or qualitative detection of at least one gas component in a measured-gas space. The gas can be, for example, an exhaust gas of an internal combustion engine, in particular in the automotive sector; and the measured-gas space can be, for example, an exhaust section. Sensor elements for detecting at least one property of gas are described, for example, in Robert Bosch GmbH: Sensoren im Kraftfahrzeug [Sensors in motor vehicles], 1st ed. 2010, pp. 98-111 and pp. 160-165. These can be, in particular, exhaust gas sensors having a variety of tasks. Binary oxygen sensors, in particular for measuring an oxygen content of the exhaust gas in the vicinity of air ratio $\lambda=1$, broadband oxygen sensors for measurement in the vicinity of air ratio $\lambda=1$ and in rich and lean exhaust gas, exhaust temperature sensors, nitrogen oxide sensors, and particle sensors are described, for example.

Exhaust gas sensors are operated in a vehicle, for example, in particular with an activation system, for example with a control unit. For this, the activation system, in particular the activation unit, has in particular a hardware module. The hardware module controls, for example, components of the exhaust gas sensor, in particular electrodes and/or heaters of the sensor element, in particular of the exhaust gas sensor.

This is done generally, depending on the complexity of the sensor element, for example using discrete electronic components, for example in the case of a binary sensor, and/or by way of discretely connected integrated electronic components, for example in the case of broadband lambda sensors or other exhaust gas sensors.

The heater can be operated, for example, on the one hand by (in particular) continuous application of a battery voltage to a vehicle ground, for example through a relay, on the other hand, for example, by cycled, in particular pulse width modulated switching of the battery voltage using a semiconductor switch, for example a "low-side" FET and/or a heater output stage, to vehicle ground. The heater output stage can be, for example, a discrete component in the activation system, in particular in the control unit, or can be contained in a multiple module. A multiple module of this kind can have in particular, besides one or more output-stage channels, further functions such as voltage supply and/or current supply and/or CAN communication and/or other functions.

The hardware module, in particular in the activation system, can be activated by a microcontroller of the activation system and in particular by the software contained therein, the so-called "hardware capsule." This software can activate the sensor element if applicable via a probe ASIC and/or can activate the heater and/or can evaluate a probe signal and/or can perform correction and/or calibration functions and/or can carry out diagnoses, and/or can deliver the probe signal to, for example, downstream software functions of the exhaust gas post-processing system.

Methods and apparatuses for avoiding incorrect operation of sensor elements, in particular exhaust gas probes, are, for example, desired. An activation system, in particular a probe activation system, with, e.g., incorrect heating voltage and/or pump voltage can result, in particular, in corruptions and/or in destruction of the sensor element. Conventional actions, in particular conventional methods, are limited in particular to a configuration of the plug connection between the sensor element, for example the exhaust gas probe, and the activation system (the control unit). Methods are available, for example, that function on the "poka-yoke" principle, for example using a "plug socket," in particular by conformation and/or coloring of, for example, a plug and/or by plug coding using at least one chip and/or at least one barcode.

Conventional methods are available, for example, for recognition of the sensor element, in particular of a sensor chip, by a shop testing unit. In a repair shop environment it is generally impossible, or possible only with difficulty, to ascertain the sensor type, in particular of the sensor element. For example, the shop testing unit in a first step can recognize, in particular independently, the sensor type; in a second step, for example, the shop testing unit can carry out a test program, in particular with no need for an operator, for example a mechanic, to input a probe type, for example a sensor type. It is thus possible to ensure, for example, that the test program and/or test parameters that is/are correct in particular for the respective sensor type can be used. It is thereby possible, for example, to reduce a number of incorrect diagnoses; for example, it is possible to prevent an intact sensor element from being recognized, in particular incorrectly, as defective.

A method and an apparatus that make possible in particular recognition of the probe type and/or of the sensor type, in particular of the sensor element, particularly preferably of the exhaust gas probe, and/or recognition of another property of, for example, an activation system, for example in a motor vehicle, would therefore be desirable.

SUMMARY

An example method and an example apparatus for operating at least one sensor element are provided, which may at least largely avoid and/or mitigate the disadvantages to be expected of conventional methods and apparatuses. "Operation of a sensor element" can be understood in particular as a method in which the sensor element is used to detect at least one property of a gas in a measured-gas space, for example in the context of a usual use of the sensor element, for example in the context of operation of a motor vehicle. Alternatively or additionally, operation can also involve, in addition to use for detection of the property, a diagnostic mode, for example in a repair shop or during a test phase.

The sensor element can in principle be any sensor element. The sensor element serves to detect at least one property of a gas in a measured-gas space, for example of an exhaust gas in an exhaust section of an internal combustion engine. The sensor element can be, in particular, an exhaust gas sensor. The sensor element can be selected, for example, from the group consisting of: at least one exhaust gas temperature sensor; at least one broadband oxygen probe; at least one binary oxygen probe; at least one nitrogen oxide sensor; at least one particle sensor; at least one lambda probe. "Detection" can be understood in particular as a measurement in which the property is ascertained qualitatively and/or quantitatively.

The property can be in principle any physical and/or chemical property of the gas. It can preferably be at least one property selected from the group consisting of: a temperature; a proportion of a gas component in the gas. The gas component can be, for example, oxygen and/or nitrogen oxides. The detection action can involve, in particular, quantitative and/or qualitative detection. The gas can be, for example, an exhaust gas of an internal combustion engine, in particular in the automotive sector. The measured-gas space can be, for example, an exhaust section. The proportion of the gas component can also refer, in particular, to multiple proportions of a gas component. The proportion of the gas component can be, in particular, a partial pressure and/or a percentage of the gas component.

The example method includes at least the following steps:
at least a first step, in the first step at least one parameter being ascertained;
at least one second step, in the second step the parameter being compared with at least one comparison value, in accordance with that comparison at least one feature being allocated to the sensor element or to at least one part of the sensor element.

The terms "first" and "second," and if present also "third" or further similar terms, give no information as to whether, for example, further steps are also present. In principle, these terms likewise provide no indication as to a sequence. Particularly preferably, the example method can be carried out in the sequence beginning with the first step, subsequently thereto the second step, and subsequently thereto, for example, further steps, but a different sequence is also possible.

A "parameter" can be understood here in general as a property of the sensor element, for example a qualitative and/or a quantitative property. The parameter can be, in particular, a characteristic magnitude. The parameter can be selected, for example, from the group consisting of: an ohmic resistance; an operating temperature; an electrical current, in particular a current characteristic curve; an electrical voltage, in particular a voltage characteristic curve.

A "comparison value" can be understood in general as at least one value, or a set of values, that can be compared with the parameter in such a way that at least one comparison result, for example a qualitative and/or quantitative comparison result, can be generated, for example a comparison result such as "corresponds to," "is greater than," "is less than," "is greater than or equal to," "is less than or equal to," "deviates by no more than a predefined value from," or the like. The comparison value can be, for example, at least one single value and/or at least one tolerance range and/or at least on range and/or at least one value table.

The at least one part of the sensor element can be, for example, the entire sensor element and/or a part of the sensor element; it can be, for example, at least one heating element and/or at least one electrode.

A "feature" can be understood in the context of the present invention in general as a property of the sensor element, in particular a property that characterizes the sensor element and/or the nature of the sensor element or of a part thereof. It can be, for example, a property that is not directly measurable, for example cannot be directly detected via an electrical measurement. The feature can be, for example, a type designation, in particular a sensor type and/or a probe type, and/or an operating duration of at least one part of the sensor element.

A "comparison" can be understood here as an analysis, for example an analysis that enables one or more of the following statements: the parameter is or is not coincident with the comparison value; the parameter is greater than the comparison value; the parameter is less than the comparison value; the parameter is greater than or equal to the comparison value; the parameter is less than or equal to the comparison value; the parameter is with a tolerance range of the comparison value. The comparison can, in particular, encompass calculation methods.

As set forth above, in accordance with this comparison the at least one feature is allocated to the sensor element or to the at least one part of the sensor element. An "allocation in accordance with the comparison" is understood in the context of the present invention to mean that the allocation is dependent on at least one result of the comparison. For example, at least one comparison result can be generated in the context of the comparison, the allocation occurring in accordance with a correlation between the comparison result and the feature to be allocated, for example according to a function, a table, a list, or similar correlations.

The example method can be used in particular to recognize the sensor type, in particular the probe type, by way of a software function in an activation system, in particular in a control unit, for example in a motor vehicle. In the first step, particularly preferably parameters of an exhaust gas sensor can be ascertained in the control unit, for example by way of an electrical test. For example, a heater resistance for different temperatures and/or a current consumption of the heater and/or a voltage consumption of the heater and/or a power consumption of the heater and/or a determination of the limit current of the reference air conduit can be carried out. The "limit current," in particular the limit current of the reference air conduit, can be understood in particular as a limited maximum current, in particular a maximum pump current, the limitation being capable of being determined in particular by diffusion, in particular by diffusion of gas particles. In a second step, the parameter of the sensor element, in particular of the exhaust gas sensor, can be compared in particular with data, in particular with the comparison values, in particular of known exhaust gas sensors, particularly preferably of different manufacturers, stored in the activation system, particularly preferably in the control unit, and can be allocated by way of the feature, for example, to an operating mode, hereinafter also called an "operating profile," that matches the feature, in particular is stored in the activation system.

The example method can in particular include a third step, in the third step at least one operating mode being capable of being selected in accordance with the at least one feature. The sensor element can then, in particular, be operated in the operating mode. An "operating mode" can be understood in the context of the present invention in general as an instruction, or a group of instructions, according to which the sensor element is operated. This instruction can include, for example, a manner in which the sensor element is impinged upon by at least one voltage and/or at least one electrical current, and/or a manner in which at least one measured value is detected at or in the sensor element, for example a manner in which at least one voltage and/or at least one current is detected at or in the sensor element. The instruction can also encompass a sequence in time of these manners of impingement and/or measurements. For example, the operating mode can also encompass operation at a defined temperature and/or a defined frequency, for example of an electrical voltage and/or of an electrical current. The "operating mode" can furthermore be understood as a circuit configuration and/or a method for operation and/or as output of an information item and/or as communication of an information item.

For example, when a replacement of the sensor element, in particular a probe replacement, is carried out, for example in a repair shop, and/or when a different sensor element, in particular a sensor element of a different probe type, is installed, the activation system, in particular the control unit, can be set and/or switched over, for example, automatically, to the operating mode required for the new sensor element, in particular to a correct operating profile. The activation system, in particular the control unit, can recognize, in particular, independently, which sensor type has been installed, and/or can independently select an appropriate operating mode, in particular an appropriate operating profile.

At least one step selected from the group consisting of the first step, the second step, and the third step can be performed at least in part by at least one activation system. An "activation system" can be understood in general as an apparatus that is set up to operate the sensor element, for example to detect the at least one property. The activation system can be configured in centralized or also decentralized fashion, and can also be integrated, for example entirely or in part, into another apparatus, for example into a control unit and/or engine control unit. The activation system can be connected, for example via an interface, to the sensor element. The activation system can, however, also be integrated entirely or in part into the sensor element. The activation system can, however, also be, for example, integrated entirely or in part into other components, for example into a plug connector and/or into an engine controller. The activation system can encompass, for example, at least one impingement apparatus for impingement of current and/or voltage onto the heater and/or onto at least one electrode. The impingement apparatus can be, for example, a voltage source and/or a current source. The activation system can furthermore, if applicable, encompass a measurement apparatus, for example a voltage measurement apparatus and/or a current measurement apparatus. The activation system can furthermore optionally encompass, for example, an evaluation apparatus, for example a data processing apparatus. The evaluation apparatus can be configured in particular to carry out the first step and/or the second step, for example the ascertaining of the parameter and/or the comparison of the parameter with the comparison value. Furthermore, the activation system can optionally encompass at least one signal generator. The activation system can moreover optionally encompass at least one regulator, for example at least one lock-in regulator. The activation system can furthermore preferably encompass at least one microcontroller and/or at least one hardware module. The activation system can furthermore be equipped with a corresponding software program that assists and/or regulates the method according to the present invention and/or serves to store and/or save the comparison value, for example in a memory.

As a result of the comparison of the parameter with the comparison value, in particular a fault situation can be recognized, and preferably in the case of recognition of a fault at least one fault message can be outputted. A "fault situation" can be understood in general as an event or a group of events that deviate from at least one predefined standard, for example from a set of standard events. The fault situation can be, for example, a situation in which the type designation of the sensor element is not known, for example because necessary data are not stored in the activation system, or it can be a situation in which the sensor element cannot be operated with the activation system. Alternatively or additionally, the fault situation can also be or can encompass a situation in which it is found in the comparison that the sensor is defective or exhibits a behavior deviating from a standard behavior, for example if the sensor element is aged.

A "fault message" is understood generally as an information item that is conveyed and/or made available to a user and/or to another unit, the content of which item is that a fault situation has occurred, and preferably also which type of fault situation is involved. The fault message can be outputted, in particular, acoustically and/or optically and/or haptically and/or electronically. The fault situation can occur, for example, if the type of the sensor element, for example the probe type, is not recognized and/or if it is recognized that the sensor element type cannot be operated with the available hardware. In this case a fault can be "set," in particular electronically, for example by the fact that a fault bit in a data memory is set to a predefined value.

As discussed above, the parameter can be compared, for example, with at least two, preferably with at least three comparison values. The comparison value can be selected, in particular, from the group consisting of: a single comparison value; a comparison range; a value table. The comparison value can be, in particular, an individual value and/or an individual value having a tolerance range. A comparison range can be, for example, an open range and/or a semi-open range and/or a closed range. For example, it can be a range extended infinitely at one end. The value table can be, in particular, a table having at least two comparison values.

The sensor element can, in particular, encompass a heating element, which is also referred to hereinafter as a "heater." The heating element can encompass, for example, at least one heating resistor. The heating element can preferably be configured to adjust and/or regulate at least one part of the sensor element to a specific temperature. The heating element can be operated, for example, by impingement of an electrical current and/or electrical voltage and/or electrical power, for example by the activation system. The parameter in this context can encompass, in particular, at least one parameter of the heating element, in particular a parameter selected from the group consisting of: a heater resistance; a heater current; a heater voltage; a heater power level.

The heater current can be, in particular, the electrical current that can be impinged onto the heating element. The heater voltage can be, in particular, the electrical voltage that can be impinged onto the heating element. The heater power level can be, in particular, the electrical power level that can be impinged onto the heating element. In principle, the parameter of the heating element can also be another physical or chemical magnitude, for example maximum and/or minimum temperatures to be reached. Particularly preferably, the parameter can encompass a heater current at a predefined heater voltage. The parameter can be compared, for example, with at least two, preferably with at least three comparison values, in particular with two ranges and one individual value.

Alternatively or additionally, the parameter can encompass, for example, at least one limit current of the sensor element or of at least one part of the sensor element. A "limit current" of a sensor element or of a part of the sensor element can be understood in general as a saturation current of the sensor element or of a part thereof, for example a saturation current of a current-voltage characteristic curve detected under predefined conditions. This current-voltage characteristic curve can be detected, for example, at a cell of the sensor element, which cell encompasses at least two electrodes and at least one solid electrolyte connecting the electrodes. The physical cause of the saturation can consist, for example, in the transport of at least one gas component respectively to and/or away from one or more of the electrodes, which can be limited, for example, by a diffusion process.

The parameter can be compared, for example, with at least three comparison values, in particular with three ranges, a feature being capable of being allocated to the sensor element in accordance with the comparison. The feature can encompass, in particular, at least one sensor element type, in particular a probe type, and/or at least one state of the sensor element, for example a defect and/or an age.

The parameter can include, for example, at least one internal resistance of the sensor element or of at least one part thereof. This internal resistance can be, for example, an internal resistance of at least one cell in accordance with the definition above and/or can be a heater resistance of at least one heating element of the sensor element. The parameter can preferably be compared with two comparison values, in particular two ranges. A feature or several features can preferably be allocated to the sensor element, for example, in accordance with the comparison, the feature being capable of encompassing, in particular, at least one sensor element type.

The parameter can include, for example, at least one internal resistance, in particular an ohmic internal resistance, the parameter being capable of being compared, for example, with at least one comparison value, in particular at least one value table. Particularly preferably, a feature can be allocated to the sensor in accordance with the comparison.

The feature can include, for example, an aging of the sensor element and/or an operating duration. In accordance with the feature, for example, a replacement of the sensor element can occur as applicable. The aforementioned fault signal can, for example, encompass an information item as to whether such a replacement is to be performed.

In a further aspect of the present invention, as set forth above, an example apparatus for detecting at least one property of a gas in a measured-gas space is proposed. The apparatus includes at least one sensor element. This can be, for example, a ceramic sensor element, for example a ceramic sensor element having at least one layer structure. The sensor element can, in particular, encompass at least one cell, which has at least two electrodes and at least one solid electrolyte connecting the electrodes. At least one of the electrodes can, for example, be capable of impingement by gas from the measured-gas space, directly or via at least one gas-permeable porous element. The sensor element can furthermore, alternatively or additionally, comprise at least one heating element and/or at least one temperature sensor. For possible embodiments of the sensor element, reference can be made, for example, to the description above and/or to Robert Bosch GmbH: Sensoren im Kraftfahrzeug [Sensors in motor vehicles], 1st ed. 2010, pp. 98-111 and pp. 160-165.

The example apparatus furthermore has at least one activation system. The activation system is set up to carry out the example method according to the present invention for operating a sensor element for detecting at least one property of a gas in a measured-gas space, as described above.

The example method according to the present invention and the example apparatus according to the present invention can have a plurality of advantages as compared with known methods and apparatuses. For example, faulty operation of and damage to the sensor element, in particular the exhaust gas sensor, due to operation with an incorrect operating profile, can preferably be precluded. In a context of initial installation, in particular manufacture, the method according to the present invention can be used, for example, to facilitate exchangeability of different sensor types. In particular, for example, the various sensor types can be configured to be compatible in hardware terms, i.e., sensor elements of different sensor types can be operated, for example, on the same hardware module. This can be advantageous, for example, for the vehicle manufacturer, since, for example, it is possible to eliminate an outlay for ensuring that the correct operating profile appropriate for the particular sensor type, in particular probe type, that is installed, in particular an appropriate operating mode and/or information about it, has been stored in the activation system, in particular in the control unit. The example method according to the present invention and/or the example apparatus according to the present invention can, for example, make it possible, in particular in production, for a different probe type, for example, to be installed from one vehicle to another without being disadvantageous, for example, subsequently during operation or in the context of repair. Thanks to the development of new, in particular digital, and/or software-configurable activation systems and/or activation concepts (ASICs), it can be possible in the future, for example, to make available hardware-compatible "open" interfaces for broadband probes as well.

BRIEF DESCRIPTION OF THE DRAWINGS

Exemplifying embodiments of the present invention are depicted in the Figures, and are explained in further detail below.

DETAILED DESCRIPTION OF EXAMPLE EMBODIMENTS

Figure 1:
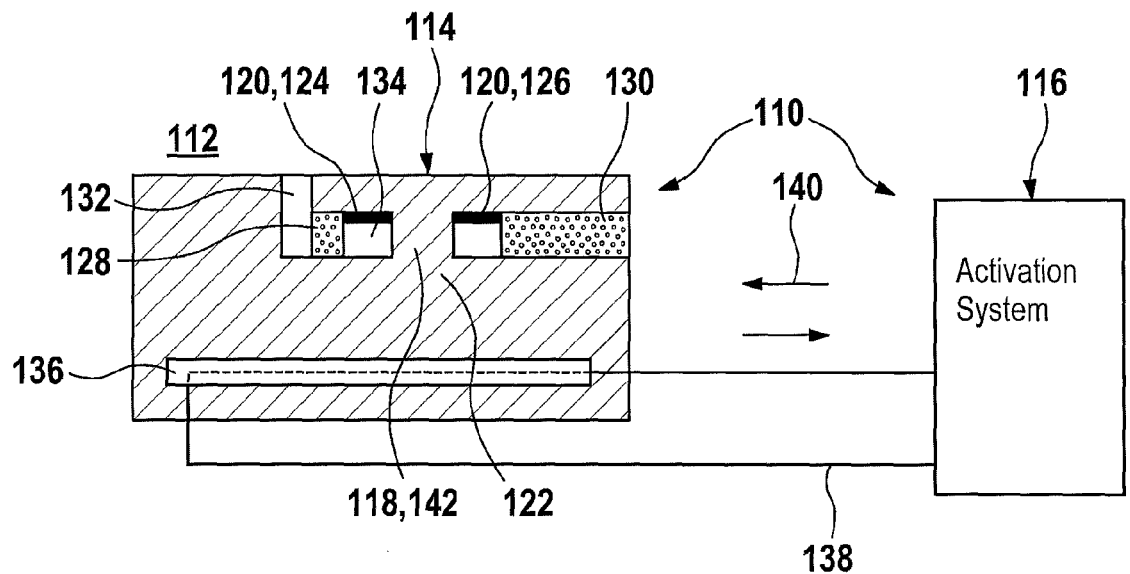
FIG. 1 shows an exemplifying embodiment of an apparatus according to the present invention.

FIG. 1 depicts an exemplifying embodiment of an apparatus 110 according to the present invention. Apparatus 110 according to the present invention for detecting at least one property of a gas in a measured-gas space 112 includes at least one sensor element 114. Apparatus 110 furthermore has at least one activation system 116. Activation system 116 is set up to carry out a method in accordance with the present invention for operating at least one sensor element 114 for detecting at least one property of a gas in a measured-gas space 112. Sensor element 114 can be configured in particular as a lambda probe. Sensor element 114 can be configured, for example, as a single-cell or multiple-cell sensor element 114. A "cell" 118 can be understood here, for example, as an assemblage of at least two electrodes 120 and a solid electrolyte 122. Solid electrolyte 122 can be, in particular a ceramic solid electrolyte 122, for example zirconium dioxide, in particular yttrium-stabilized zirconium dioxide (YSZ) and/or scandium-doped zirconium dioxide (ScSZ). Solid electrolyte 122 can preferably be gas-impermeable, and/or can ensure ionic transport, for example ionic oxygen transport. Sensor element 114 encompasses at least one first electrode 124 and at least one second electrode 126. First electrode 124 can be connected at least in part, in particular via a diffusion barrier 128, to measured-gas space 112. Second electrode 126 can be connected at least in part to a further gas space, in particular to a reference-gas space, for example a reference conduit 130. Reference conduit 130 can be connected in particular to an air reservoir, in particular to outside air. First electrode 124 can be impinged upon by gas from measured-gas space 112, in particular via a gas access path 132 and/or via diffusion barrier 128. An electrical voltage, in particular a Nernst voltage, can be measured between first electrode 124 and second electrode 126. Based on the Nernst voltage, conclusions can be drawn, for example, as to the proportion of the gas component in the gas, in particular in the exhaust gas. The proportion of the gas component can be, for example, a partial pressure of the gas component; it can be, in particular, an oxygen partial pressure and/or an oxygen proportion. The gas component can particularly preferably be oxygen. In principle, the gas component can also encompass at least one nitrogen oxide. The Nernst voltage is, in particular, as a rule dependent on a difference in the concentration of the gas component between first electrode 124 and second electrode 126. Sensor element 114 depicted in FIG. 1 represents, in particular, a single-cell sensor element 114. In principle, single-cell or also multiple-cell sensor elements 114 can be used, as described, e.g., in Robert Bosch GmbH: Sensoren im Kraftfahrzeug [Sensors in motor vehicles], 1st ed. 2010, pp. 160-165. Second electrode 126 can be configured in particular as a reference electrode. First electrode 124 can be disposed in a cavity 134, but can also be connected fluidically and/or via a gas connection to cavity 134. In addition, sensor element 114 can encompass a heating element 136, in particular a heater. Heating element 136 can be connected in particular via electrical lines 138 to activation system 116. Activation system 116 can be connected, for example, via an interface 140 to sensor element 114. Activation system 116 can, however, also be integrated entirely or in part into sensor element 114. Activation system 116 can, however, also, for example, also be integrated entirely or in part into other components, for example into a plug connector and/or into an engine controller. Activation system 116 can, for example, encompass at least one impingement apparatus for impingement of current and/or voltage onto electrodes 120, for example first electrode 124 and/or second electrode 126. The impingement apparatus can be, for example, a voltage source and/or a current source. The impingement apparatus can encompass, in particular, electrical leads 138. The impingement apparatus can, for example, in particular encompass electrical leads 138 to heating element 136, in particular for supplying electrical voltage and/or electrical current to heating element 136. Activation system 116 can, if applicable, encompass at least one measurement apparatus, for example at least one voltage measurement apparatus and/or at least one current measurement apparatus. Activation system 116 can furthermore optionally encompass, for example, at least one evaluation apparatus, for example at least one data processing apparatus. Furthermore, optionally, activation system 116 can encompass at least one signal generator. Activation system 116 can moreover optionally encompass at least one regulator, for example at least one lock-in regulator. Activation system 116 can furthermore contain, for example, at least one microcontroller and/or at least one hardware module and/or at least one software program and/or a memory, in particular a data memory.

The example method according to the present invention for operating a sensor element 114 for detecting at least one property of a gas in a measured-gas space 112 includes at least the following steps: at least one first step, in the first step at least one parameter being ascertained; at least one second step, in the second step the parameter being compared with at least one comparison value, in accordance with that comparison at least one feature being allocated to sensor element 114 or to at least one part of sensor element 114.

The method can, in particular, include a third step, in the third step an operating mode being capable of being selected in accordance with the feature, sensor element 114 being operated in the operating mode. The method can also include one or more further steps, the steps being capable, for example, of also being carried out repeatedly and/or in different sequences.

At least one step, selected from the group consisting of the first step, the second step, the third step, and optionally a further step, can be executed at least in part by the at least one activation system 116. For example, on the basis of the comparison of the parameter with the comparison value a fault situation can be recognized, and in the event of recognition of a fault, preferably at least one fault message can be outputted.

In a first exemplifying embodiment, the parameter can be selected in particular from the group consisting of: a heater current; a heater voltage; a heater power level. Sensor element 114 can encompass in particular a heating element 136, particularly preferably a heater. Heating element 136 can, in particular in the context of a cold sensor element 114, for example at the beginning of operation of sensor element 114, for example after an operating down time and/or upon initial operation, be switched on, for example, for 1 ms to 1 s, in particular 50 ms to 150 ms, particularly preferably for approx. 100 ms. At the same time and/or thereafter, for example, the parameter, in particular the heater current $I_H$, can be measured. Measurement of the heater current can be performed, in particular, within the first step. The heater current can be detected, in particular, continuously, but also, for example, only one or several values of the heater current can be detected. In particular, heating element 136 can in this context be operated at a predefined heater voltage and/or a predefined temperature, in particular an electrical voltage. In the second step, the comparison can include in particular an evaluation of the parameter. For example, it can be concluded from a heater current $I_H$<2.2 A that a controlled heater operating mode can in particular exist. A sensor type can also, in particular, be inferred from the parameter. The controlled heater operating mode can be, for example, operation of a two-point lambda probe, in particular a binary probe. For $I_H$>2.2 A, for example, cycled heater operation can be inferred. This can likewise, for example, allow inference of a two-point lambda probe, in particular a binary probe, in particular sensor element 114 being capable of being a binary probe having, in particular, fast regulation readiness and/or a strong heater element 136, in particular a strong heater. The probe can also, however, for example, be a broadband lambda probe. For $I_H$=0 it can be concluded that, for example, sensor element 114 and/or an output stage and/or a wiring harness are defective. The parameter can therefore, for example, include a heater current at a predefined heater voltage, the parameter being capable of being compared with at least two, preferably with at least three comparison values, in particular two ranges and one individual value. The parameter can also encompass an electrical current and/or an ohmic resistance and/or a temperature. In this exemplifying embodiment, the example method according to the present invention can in particular result in recognition of a controlled and/or regulated heater operating mode by detection of a switch-on current of heating element 136, in particular of the heater.

In a second exemplifying embodiment, the parameter can include, for example, at least one limit current of sensor element 114 or of at least one part of sensor element 114, for example a limit current of reference conduit 130 and/or a limit current of diffusion barrier 128. For this, for example, in the first step the parameter, in particular the limit current, particularly preferably the limit current of reference conduit 130, for example the limit current of the reference air conduit (IgRK), can be measured. For this, a heating power level of, for example 8 W can be applied, in particular, to heating element 136. Furthermore, for example, a voltage 800 mV can be impinged, for example applied, between a reference electrode, for example a negative pole, particularly preferably an electrode 120, for example second electrode 126, and an internal pump electrode, for example as a positive pole, in particular an electrode 120, particularly preferably a first electrode 124. The limit current can be detected directly, but alternatively or additionally can also, for example, be measured after a time to be applied. The parameter, in particular the limit current, can be detected, for example, continuously, for example as a parameter curve, or by way of one or more individual values. A "limit current" IgRK of reference conduit 130 can be understood here, for example, as a maximum electrical current, in particular a pump current, limited by diffusion of the gas component, for example of gas particles, in particular of oxygen. The limit current can be measured, for example, by applying an electrical voltage, in particular between two electrodes 120, in particular between first electrode 124 and second electrode 126. In particular at low voltage, the proportion of the gas component, in particular the proportion of oxygen, can be, in particular, proportional to the applied voltage. When the limit current of reference conduit 130 is reached, a saturation can particularly preferably occur. Electrodes 120 can particularly preferably be a reference electrode and an external pump electrode. Particularly preferably, the parameter can be the pump current and/or the limit current. In the second step, in particular, an evaluation can occur. For $0.1 < \text{IgRK} < 10$ μA, for example, a broadband lambda probe can be inferred. This can involve, in particular, a sensor element 114 having a heating element 136. Heating element can be configured here in particular with a higher heating power level than comparable broadband lambda probes. For $300 \text{ μA} < \text{IgRK} < 800$ μA, the probe can in particular once again be a broadband lambda probe. This can involve, in particular, a broadband lambda probe having a heating element 136 having a lower heating power level as compared with other broadband lambda probes. Upon the occurrence of limit currents, in particular ones deviating from the aforementioned comparison values, of reference conduit 130, a defective sensor element 114 can, in particular, be inferred. The comparison value can include here, in particular, at least three ranges. In this second exemplifying embodiment, a distinction can be made in particular between sensor elements 114, in particular sensors, having an air reference, and sensor elements 114, in particular sensors, having a pumped reference, as in the second case. It is thus possible in particular to infer a sensor type, in particular as a feature. It is furthermore possible to diagnose, for example, a probe defect by way of the limit current of reference conduit 130, in particular the limit current of the reference air conduit.

In a third exemplifying embodiment the parameter can include, for example, at least one internal resistance, in particular at least one ohmic internal resistance, of the sensor 114 or of at least one part thereof, for example at least one internal resistance of a Nernst cell 142. In particular, recognition of the sensor can occur by way of at least one internal resistance of a Nernst cell 142. A Nernst cell 142 can be, in particular, a cell 118. A Nernst cell 142 can encompass, in particular, at least two electrodes 120, in particular first electrode 124 and second electrode 126, and solid electrolyte 122. The sensor types can differ, for example, in terms of an ohmic resistance RiN of Nernst cell 142, in particular for identical heater voltages. One broadband lambda probe can have, for example, a resistance $\text{RiN}=300\Omega$ of Nernst cell 142, a different broadband lambda probe, in particular having a different configuration, in particular a different sensor type, being capable of having a resistance $\text{RiN}=800\Omega$ of Nernst cell 142. Application of a constant voltage through Nernst cell 142, for example between two electrodes 120, in particular between, for example, first electrode 124 and second electrode 126, particularly preferably between the reference electrode and the internal pump electrode, can result in particular in currents, in particular pump currents, of different magnitudes, for example as a result of different resistances. As a result, the resistance, in particular the internal resistance, of Nernst cell 142 is particularly suitable as a parameter. For example, in particular a constant heating power level can be applied to heating element 136, preferably while the vehicle is stationary. Flow to the probe, in particular to sensor element 114, can thereby, for example, be prevented. In that context and/or thereafter, for example after a waiting time, the resistance RiN of Nernst cell 142, in particular the internal resistance, can be measured. The parameter, here the internal resistance, can thereby, in particular, be detected. During the second step, in particular, an evaluation can be carried out. If RiN is, for example, lower than a threshold, the probe can be, for example, a broadband lambda probe having a specific sensor type. If RiN is greater than a threshold, the probe can be, for example, a broadband lambda probe of a different probe type. A comparison value can in principle also encompass a threshold, in particular a threshold value, for example as in this exemplifying embodiment. In this exemplifying embodiment the feature is, in particular, a sensor type. The sensor type can be recognized, for example, by way of the internal resistance of Nernst cell 142. This can serve, for example, in a third step, for selection of an operating mode in accordance with the feature, i.e., the sensor type, sensor element 114 being capable of being operated, in particular, in that operating mode.

Figure 2:
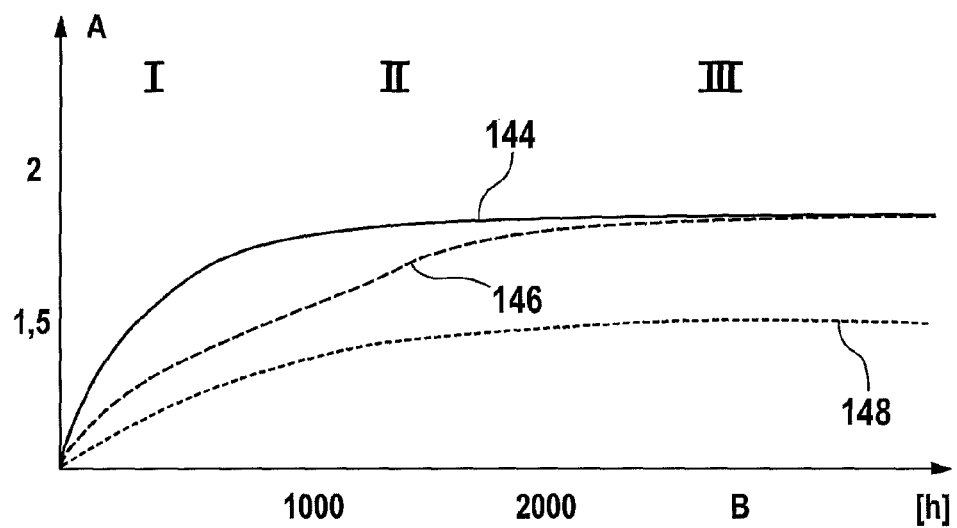
FIG. 2 shows an exemplifying embodiment of a method according to the present invention for operating at least one sensor element.

FIG. 2 depicts, for example, a fourth exemplifying embodiment of the method according to the present invention. The parameter here can include at least one internal resistance, for example at least one alternating current resistance, in particular at least one impedance and/or at least one reactance and/or at least one effective resistance and/or at least one direct current resistance. Aging of the internal resistance, in particular of the alternating current internal resistance, of Nernst cell 142 (RiAC) can have the result, in particular, that for the same temperature, in particular for the same ceramic temperature, the internal resistance rises with operating duration and/or with age. In a broadband lambda probe the internal resistance in new condition at a ceramic temperature of 780° can be, for example, nominally $300\Omega$. After operation, in particular during continuous engine operation, for example for 3000 hours, at preferably the same, in particular a constant ceramic temperature, the internal resistance can be equal in particular to up to $500\Omega$. With apparatus 110 according to the present invention and with the method according to the present invention, using this parameter, in particular this property, it is possible to identify, in particular in the control unit, whether, for example, an old sensor element 114, in particular an old probe, has been replaced with a new sensor element 114, in particular a new probe. If applicable, the operating mode, in particular an operating profile, can be modified and/or adapted. In a first step, for example, an, in particular, constant heating power level can be applied with the vehicle stationary. This can prevent, for example, flow to sensor element 114. The parameter, in particular the alternating current internal resistance RiAC of Nernst cell 142, can be detected. This exemplifying embodiment can be carried out in particular using a broadband lambda probe. A broadband lambda probe can encompass in particular at least two cells 118, preferably at least one Nernst cell 142 and/or at least one pump cell. The pump cell can preferably have at least one externally located electrode 120, Nernst cell 142 preferably being capable of having at least one internally located electrode 120. In principle, this exemplifying embodiment can also be carried out with other sensor elements 114, in particular with a two-point lambda probe, for example a binary probe, for example a binary probe having fast regulation readiness and/or a strong heating element 136. In the second step a correlation of the internal resistance RiAC with service life, in particular the service life of sensor element 114, in particular at a constant heating power level of heating element 136 and with or without flow to sensor element 114, can be taken in particular from a value table. From the parameter, in particular the internal resistance, conclusions can be drawn in particular as to the operating duration of sensor element 114, in particular of the probe.

An even more accurate determination of aging can be made preferably by way of a determination of the aging of a direct current internal resistance RiDC, in particular of electrodes 120, in particular of the internally and externally located electrodes, for example of a pump cell and/or of a Nernst cell 142. The following basic principles can be utilized here, for example: RiDC, which can in particular describe an electrode degradation, ages in particular, as a rule, more quickly and/or with a higher factor, in particular an aging factor A, than RiAC. In this first step, for example, an alternating current having a frequency of, for example, 4 kHz can be applied. As a rule, only the electrolyte degradation is measured in this context. The cause of this can be, in particular, that the electrode/electrolyte transitions, described in particular as a parallel circuit of a capacitor and a resistor, can preferably be "bridged" by the capacitor, since in the context of an alternating current measurement the resistance, in particular the real portion of the resistance, cannot concurrently be measured.

FIG. 2 depicts, in particular, an aging factor A with respect to an operating time B in hours (h). The operating time is depicted here, in particular, subdivided into three different phases that are labeled I, II, and III. The upper curve 144 describes, in particular, the aging factor of an RiDC, for example of one or more externally located electrodes 120, in particular electrodes 120 of a pump cell, the middle curve 146 being capable of depicting the aging factor of an RiDC, for example of one or more internally located electrodes 120, in particular electrodes 120 of Nernst cell 142. The lower curve 148 shows, in particular, the aging factor of RiAC, in particular in the context of an alternating voltage and/or an alternating current of 4 kHz, for the internally located electrodes 120 and/or externally located electrodes 120. The RiDC, in particular the RiDC of at least one externally located electrode 120, in particular of one or more electrodes 120 of the pump cell, ages, in particular, more quickly than that of one or more internally located electrodes 120, in particular of electrodes 120 of a Nernst cell 142. A high aging factor can be interpreted, in particular, as high aging. The difference between the internal direct current resistance values of the externally located electrodes 120 and the internally located electrodes 120 can be caused, in particular, by penetration of damaging exhaust gas constituents, since, for example, penetration is limited substantially only by a protective layer and not by a diffusion barrier 128. Aging of the RiAC can occur in particular in the interior of the electrolyte, in particular of solid electrolyte 122, and can thus be, in particular, independent of damage thereto by exhaust gas constituents. This aging can be, in particular, principally a temperature effect and can thus proceed almost identically, for example, for electrodes 120 and/or cells 118, in particular for both cells 118 of a two-cell sensor element 114. In principle, the aging, independently of the as-new value, can be relative to the as-new value in each case by a factor, in particular the aging factor A. From this knowledge in particular, a rough categorization and/or allocation of the service life and/or operating duration, for example to sensor element 114, can be achieved. FIG. 2 depicts, for example, comparison values for service lives<500 h, for example for service lives between 500 and 100 h, and, for example, for service lives>1000 h. In Phase I, the RiDC in particular of one or more externally located electrodes 120, in particular the RiDC of the pump cell, can already be aged. Phase I can extend, for example, between 0 h and 500 h. In phase II, the RiDC in particular of one or more internally located electrodes 120, in particular the RiDC of Nernst cell 142, can be aged, i.e., after an operating time of, for example, 500 h to 1000 h. In phase III, in particular the RiAC, in particular for all electrodes 120, for example for externally located electrodes 120 and internally located electrodes 120, can be greatly aged, for example after an operating time of more than 1000 h. The method according to the present invention may require in particular, for example as a comparison value, an empirical factor for RiDC aging, which can describe, for example, an intensity of poisoning as a result of the respective application.

What is claimed is:

1. A method for operating at least one sensor element for detecting at least one property of a gas in a measured-gas space, the method comprising:
    ascertaining at least one parameter, which includes a qualitative property and a quantitative property of the sensor element; and
    comparing the parameter with at least one comparison value, at least one feature being allocated to one of the sensor element or to at least one part of the sensor element, in accordance with the comparison;
    wherein the at least one feature includes one of a type designation, a sensor type, a probe type, and an operating duration of at least one part of the sensor element, and
    wherein the allocation is dependent on at least one result of the comparison, and
    wherein the qualitative property is a property that is not directly measurable via an electrical measurement, and
    wherein the at least one parameter of the sensor element is compared with comparison values of known exhaust gas sensors stored in the activation system, and is allocated to an operating mode or an operating profile that matches a corresponding one stored in the activation system.

2. The method as recited in claim 1, wherein the parameter is compared with at least two comparison values.

3. The method as recited in claim 1, wherein the parameter is compared with at least three comparison values.

4. The method as recited in claim 1, wherein the comparison value is selected from a group consisting of: a single comparison value, a comparison range, a value table.

5. The method as recited in claim 1, wherein the sensor element includes a heating element, the parameter includes at least one parameter of the heating element, the parameter being selected from a group consisting of: a heater resistance, a heater current, a heater voltage, a heater power level.

6. The method as recited in claim 1, wherein the parameter includes a heater current at a predefined heater voltage, the parameter being compared with at least two comparison values.

7. The method as recited in claim 1, wherein the parameter includes a heater current, the parameter being compared with at least three comparison values with two ranges and one individual value.

8. The method as recited in claim 1, wherein the parameter includes at least one limit current of one of: i) the sensor element, or ii) at least one part of the sensor element.

9. The method as recited in claim 1, wherein the parameter includes at least one internal resistance of one of: i) the sensor element, or ii) at least one part of the sensor element.

10. The method as recited in claim 1, wherein the feature includes at least one of an aging of the sensor element, and an operating duration of the sensor element.

11. The method as recited in claim 1, further comprising:
   selecting an operating mode in accordance with the feature, the sensor element being operated in the operating mode.

12. The method as recited in claim 11, wherein at least one of the ascertaining step, comparing step, and selecting step are performed at least in part by at least one activation system.

13. The method as recited in claim 11, further comprising:
   on the basis of the comparison of the parameter with the comparison value, recognizing a fault situation, and in the case of recognition of a fault situation, outputting at least one fault message.

14. An apparatus for detecting at least one property of a gas in a measured-gas space, comprising:
   at least one sensor element; and
   at least one activation system configured to ascertain at least one parameter, which includes a qualitative property and a quantitative property of the sensor element, and to compare the parameter with at least one comparison value, at least one feature being allocated to one of the sensor element or to at least one part of the sensor element in accordance with the comparison;
   wherein the at least one feature includes one of a type designation, a sensor type, a probe type, and an operating duration of at least one part of the sensor element, and
   wherein the allocation is dependent on at least one result of the comparison, and
   wherein the qualitative property is a property that is not directly measurable via an electrical measurement, and
   wherein the at least one parameter of the sensor element is compared with comparison values of known exhaust gas sensors stored in the activation system, and is allocated to an operating mode or an operating profile that matches a corresponding one stored in the activation system.

15. The apparatus as recited in claim 14, wherein the parameter is compared with at least two comparison values.

16. The apparatus as recited in claim 14, wherein the parameter is compared with at least three comparison values.

17. The apparatus as recited in claim 14, wherein the comparison value is selected from a group consisting of: a single comparison value, a comparison range, a value table.

18. The apparatus as recited in claim 14, wherein the sensor element includes a heating element, the parameter includes at least one parameter of the heating element, the parameter being selected from a group consisting of: a heater resistance, a heater current, a heater voltage, a heater power level.

19. The apparatus as recited in claim 14, wherein the parameter includes a heater current at a predefined heater voltage, the parameter being compared with at least two comparison values.

20. The apparatus as recited in claim 14, wherein the parameter includes a heater current, the parameter being compared with at least three comparison values with two ranges and one individual value.

21. The apparatus as recited in claim 14, wherein the parameter includes at least one limit current of one of: i) the sensor element, or ii) at least one part of the sensor element.

22. The apparatus as recited in claim 14, wherein the parameter includes at least one internal resistance of one of: i) the sensor element, or ii) at least one part of the sensor element.

23. The apparatus as recited in claim 14, wherein the feature includes at least one of an aging of the sensor element, and an operating duration of the sensor element.

24. The apparatus as recited in claim 14, wherein an operating mode is selected in accordance with the feature, the sensor element being operated in the operating mode.

25. The apparatus as recited in claim 24, wherein at least one of the ascertaining, the comparing, and the selecting are performed at least in part by at least one activation system.

26. The apparatus as recited in claim 24, wherein based on the comparison of the parameter with the comparison value, a fault situation is recognized and at least one fault message is output.

* * * * *